(12) United States Patent
Mayhew et al.

(10) Patent No.: US 7,829,523 B2
(45) Date of Patent: Nov. 9, 2010

(54) METHOD FOR STABILIZING POLYPEPTIDES LACKING METHIONINE

(75) Inventors: James Mayhew, San Francisco, CA (US); Hali Wagner, Rohnert Park, CA (US)

(73) Assignee: Dow Pharmaceutical Sciences, Petaluma, CA (US)

( * ) Notice: Subject to any disclaimer, the term of this patent is extended or adjusted under 35 U.S.C. 154(b) by 164 days.

(21) Appl. No.: 12/069,745

(22) Filed: Feb. 13, 2008

(65) Prior Publication Data

US 2008/0139454 A1    Jun. 12, 2008

Related U.S. Application Data

(62) Division of application No. 11/352,129, filed on Feb. 10, 2006, now abandoned.

(51) Int. Cl.
*A61K 38/00* (2006.01)
*C07K 14/00* (2006.01)

(52) U.S. Cl. .......................... 514/1.1; 530/300; 530/350
(58) Field of Classification Search ........................ None
See application file for complete search history.

(56) References Cited

U.S. PATENT DOCUMENTS

| 5,272,135 | A |   | 12/1993 | Takruri |
|-----------|---|---|---------|---------|
| 5,358,708 | A | * | 10/1994 | Patel ......................... 424/85.1 |
| 5,837,838 | A |   | 11/1998 | Reed |
| 6,525,102 | B1|   | 2/2003  | Chen |
| 6,734,162 | B2|   | 5/2004  | Van Antwerp et al. |
| 2003/0103895 | A1 | | 6/2003 | Cyr |

OTHER PUBLICATIONS

Baggiolini, M., et al. 1989 J Clin Invest 84: 1045-1049.*
Levine, R.L. et al. 1999 Mechanisms of Ageing and Development 107: 323-332.*
Rothstein, et al, "Anticandida activity is retained in P-113, a 12-amino-acid fragment of Histatin 5", Antimicrobial Agents and Chemotherapy, 45(5):1387-1373 (2001).

* cited by examiner

*Primary Examiner*—Maryam Monshipouri
*Assistant Examiner*—Marsha M Tsay
(74) *Attorney, Agent, or Firm*—Howard Eisenberg, Esq.

(57) ABSTRACT

Methionine is an effective antioxidant for polypeptides having an amino acid sequence lacking methionine. Compositions containing polypeptides having an amino acid sequence that is free of methionine residues are stabilized from oxidative degradation by combining methionine in the composition in an amount effective to inhibit oxidation of the polypeptide.

12 Claims, No Drawings

METHOD FOR STABILIZING POLYPEPTIDES LACKING METHIONINE

This application is a divisional application claiming priority from U.S. patent application Ser. No. 11/352,129, which was filed on Feb. 10, 2006 now abandoned.

FIELD OF THE INVENTION

The invention pertains to the field of stabilizing, such as by inhibiting the oxidation of, a polypeptide in a liquid or semi-solid medium.

BACKGROUND OF THE INVENTION

Liquid or semi-solid formulations containing one or more polypeptides are typically subject to degradation during storage, such as due to oxidation. It has been found to be difficult or even impossible to prepare and package a peptide-containing formulation so as to guarantee that oxidants, atmospheric oxygen and formulation excipients bearing residual oxidants, will be excluded. Oxygen and residual oxidants cause rapid oxidation of many of the amino acid residues in a polypeptide.

Methionine is an amino acid residue that is vulnerable to oxidation. In the presence of oxidants, methionine is rapidly oxidized to methionine sulfoxide. Takruri, U.S. Pat. No. 5,272,135 discloses that adding methionine to a liquid or semi-solid medium containing a methionine-containing polypeptide is effective to inhibit the oxidation of methionine residues in the polypeptide to methionine sulfoxide. According to the method of Takruri, methionine is added to a pharmaceutical preparation comprising a methionine-containing polypeptide in a quantity sufficient to inhibit the oxidation of methionine residues to methionine sulfoxide.

Many pharmaceutically active polypeptides exist that lack methionine residues. An example of one such polypeptide is P-113, a 12-amino acid polypeptide fragment of histatin 5 that has antimicrobial activity against *Candida* spp. and that has been used topically to treat atopic dermatitis. See, Rothstein, et al, *Antimicrobial Agents* and *Chemotherapy*, 45(5): 1367-1373 (2001). As disclosed in Rothstein, the P-113 polypeptide has an amino acid sequence that lacks methionine.

Methionine-free polypeptides such as P-113 often contain amino acids that are subject to oxidation and, therefore, although these polypeptides lack methionine, they also tend to degrade in the presence of oxygen. A substantial need exists for a method to stabilize polypeptides in liquid or semi-solid pharmaceutical formulations wherein the polypeptides have an amino acid sequence that is free of methionine.

DESCRIPTION OF THE INVENTION

It has been unexpectedly discovered that methionine is an effective antioxidant for polypeptides lacking a methionine residue. Thus, methionine is effective in stabilizing polypeptides against oxidation even when the polypeptide has an amino acid sequence that is free of methionine.

In a first embodiment, the invention is a method for inhibiting degradation, such as due to oxidation, of a liquid or semi-solid composition containing a polypeptide having an amino acid sequence that does not include methionine which method includes combining methionine in the composition in an amount sufficient to inhibit oxidation of the polypeptide.

In another embodiment, the invention is a liquid or semi-solid composition containing (1) a polypeptide having an amino acid sequence free of methionine and (2) methionine at a concentration that is sufficient to inhibit oxidation of the polypeptide.

In accordance with the invention, the methionine stabilizes the composition containing the methionine-free polypeptide by inhibiting the oxidation of amino acids in the polypeptide that are subject to oxidation. The polypeptide that is protected from oxidation by the presence of methionine is any polypeptide which contains amino acids other than methionine that are subject to oxidation and which does not contain methionine as part of the amino acid sequence of the polypeptide.

The methionine-free polypeptide may be of any length. For example, the polypeptide may be P-113, a polypeptide that is 12 amino acids in length. The polypeptide that is stabilized by the method of the invention may be as short as 3 amino acids in length or as long as 100 amino acids or more in length. For example, the polypeptide may be between 6 and 50 amino acids in length. Alternatively, the polypeptide may be between 10 and 35 amino acids in length. The invention is illustrated herein using a polypeptide that is 12 amino acids in length. With increasing length of polypeptide, higher relative concentrations of methionine to polypeptide on a molar basis are required to provide optimal antioxidation protection. However, the relative concentration of methionine to polypeptide on a weight/weight basis is not necessarily changed with change in length of the polypeptide. For example, as described in further detail in the Examples below, with a concentration of P-113 of 0.01% w/w (0.064 mM), the optimal concentration of methionine to protect against oxidative degradation due to extremely high oxidative stress related to high concentrations of hydrogen peroxide was found to be 0.2% w/w (13.42 mM), which is a molar ratio of 209.7:1 (methionine:polypeptide).

In accordance with the method of the invention, it has been found that a higher level of protection of a polypeptide against oxidative degradation is obtained by increasing the relative proportion of methionine to the polypeptide in a composition. Thus, if only minimal protection against oxidative degradation is desired, a very low ratio of methionine:polypeptide may be utilized. Higher relative concentrations of methionine:polypeptide provide a higher degree of protection.

In accordance with the invention, the concentration of methionine in a composition containing a polypeptide lacking methionine is that which is effective to inhibit the oxidation of the polypeptide in the composition in comparison to the inhibition of the polypeptide in the composition without methionine. It is conceived that the relative molar concentrations of methionine:polypeptide that are optimal in accordance with the invention are 10:1 and higher. However, molar ratios lower than 10:1 may also be used, if desired, although protection against oxidative degradation provided by such a low relative concentration of methionine may be less than optimal. Relative molar concentrations of even 1:1 or lower may also be used in accordance with the invention, provided that such low relative concentrations are effective in reducing the amount or rate of oxidative degradation of the polypeptide in a composition compared to the amount or rate of oxidative degradation in a similar composition lacking methionine. For many polypeptides, the optimal relative molar concentration of methionine:polypeptide is about 100:1 or higher. The optimal ratio is increased with polypeptides having a relatively high proportion of reactive amino acids such as tryptophan, phenylalanine, tyrosine, histidine, arginine, and lysine, and is decreased with polypeptides having a relatively low proportion of reactive amino acids. Therefore, preferably the molar ratio of methionine:polypeptide is 100:1 or higher, and more preferably, the ratio is 200:1 or higher. If desired, molar ratios as high as 500:1, or 1000:1, or even 1500:1 or higher may be employed.

The composition of the invention is typically an aqueous composition. It may be a solution, typically an aqueous solution, or a suspension, such as an oil-in-water emulsion. The composition may contain optional ingredients in addition to the methionine and polypeptide. For example, the composition may contain one or more additional polypeptides, and such additional polypeptides may have an amino acid sequence containing methionine. Such compositions containing methionine-containing polypeptides in addition to methionine-free polypeptides are included within the scope of the invention as long as the concentration of methionine in the composition is at a level which is sufficient to inhibit degradative oxidation of the methionine-free polypeptide in the composition. In a preferred embodiment, the composition is free of polypeptides that have an amino acid sequence that contains methionine.

Other optional ingredients include non-polypeptides active pharmaceutical ingredients and various inactive ingredients. Such inactive ingredients may include gelling agents such as cellulosic polymers like hydroxyethyl cellulose and carboxyvinyl polymers, such as CARBOPOL® 934, 940, and 941 (Noveon, Inc., Akron, Ohio, USA). The composition may contain preservatives such as methylparaben, propylparaben, and quaternary ammonium compounds, emulsifiers such as acrylates/C10-C30 alkyl acrylate crosspolymers, glyceryl stearate, polyethylene glycol, cetearyl alcohol, and cetearyl glucoside, pH adjusting agents such as sodium hydroxide and hydrochloric acid, a buffering system such as bicarbonate plus hydroxyethyl piperidine ethanesulfonic acid ("HEPES"), stabilizing agents such as EDTA, emollients such as petrolatum, mineral oil, and non-petroleum-based oils, surfactants, and solvents such as propylene glycol. If desired, the composition may contain antioxidants in addition to the methionine, such as glutathione or ascorbate.

The invention is further illustrated in the following non-limiting examples. The examples that follow illustrate the invention with a 12-amino acid polypeptide, P-113. The invention however is not so limited and is useful for inhibiting degradation of any polypeptide that is subject to oxidative degradation and that does not contain the amino acid methionine. The P-113 polypeptide is merely an example to illustrate that methionine is an effective antioxidant for polypeptides having an amino acid sequence that is free of methionine. For example, additional polypeptides that do not contain methionine and which are able to be protected from oxidative degradation by the method of the invention include the synthetic neurotransmitter analog of Substance P, (Nle11)-Substance P(CAS No. 57462-42-7) and the neurotransmitter-like hypothalamic polypeptide neurotensin (CAS No. 58889-67-1).

EXAMPLE 1

Oxidative Degradation of P-113

Three groups of identical aqueous compositions containing 0.01% w/w (0.064 mM) P-113 polypeptide were made. The first and second groups contained either 3% w/w (882 mM) or 5% w/w (1,470 mM) hydrogen peroxide ($H_2O_2$), a powerful oxidizing agent. The third group of compositions was a control group and contained no hydrogen peroxide. The compositions were stored at room temperature and were tested at varying intervals to determine the degree of oxidative degeneration of the polypeptide. The results are shown in Table 1.

TABLE 1

P-113 Recovery from Hydrogen Peroxide Aqueous Solutions

| Time in Hours | Control | P-113 Recovery % | |
| --- | --- | --- | --- |
| | | 3% $H_2O_2$ | 5% $H_2O_2$ |
| 0 | 100 | — | — |
| 21 | 99.3 | 67.6 | 60.5 |
| 24 | 99.6 | 60.8 | 51.4 |
| 48 | 99.5 | 55.8 | 38.6 |
| 60 | 100.2 | 51.9 | 30.6 |

As shown in Table 1, the degradation of the polypeptide was proportional to the concentration of $H_2O_2$. After 72 hours, the P-113 was degraded about 50% in the 3% $H_2O_2$ composition and about 70% in the 5% $H_2O_2$ composition. In the control composition containing no $H_2O_2$, the P-113 polypeptide showed no degradation after 72 hours.

EXAMPLE 2

Oxidative Degradation of P-113 in the Presence of Methionine

Compositions similar to the compositions of Groups 1 and 2 of Example 1 were made but with varying concentrations of added methionine. Because the majority of the degradation of P-113 when exposed to $H_2O_2$ occurred within 24 hours, this time period was evaluated to determine the protective capability of methionine. Additionally, the degradation of P-113 when exposed to 3% $H_2O_2$ for 48 hours was also evaluated. Data is shown in Table 2.

TABLE 2

P-113 Recovery from Hydrogen Peroxide Aqueous Solutions Containing Methionine

| Time in Hours | Methionine % w/w | Methionine mM | mM Met/ mM P-113 | P-113 Recovery % | |
| --- | --- | --- | --- | --- | --- |
| | | | | 3% $H_2O_2$ | 5% $H_2O_2$ |
| 24 | 0.1 | 6.71 | 104.8 | 79.2 | 70.9 |
| | 0.2 | 13.42 | 209.7 | 80.8 | 80.9 |
| | 0.3 | 20.13 | 314.5 | 81.3 | 78.7 |
| | 0.4 | 26.84 | 419.4 | 81.1 | 80.1 |
| | 0.5 | 33.55 | 524.2 | 81.8 | 79.3 |
| 48 | 0.2 | 13.42 | 209.7 | 76.6 | |
| | 0.3 | 20.13 | 314.5 | 76.8 | |
| | 0.4 | 26.84 | 419.4 | 77.2 | |

As shown in Table 2, the optimum concentration of methionine to protect a 0.01% (0.064 mM) P-113 composition is about 0.2% w/w (13.42 mM) or higher. When a 0.1% w/w (6.71 mM) methionine concentration was used with a 3% hydrogen peroxide concentration, the recovery of P-113 was slightly lower than in the formula containing 0.2% methionine. However, the solution containing 0.1% methionine and 5% hydrogen peroxide showed a distinct decrease in P-113 recovery compared to the formula containing 0.2% or higher methionine. It is also noted that the recovery of P-113 was not substantially increased when the methionine concentration was increased above 0.2% w/w (13.42 mM). This data indicates that, at the concentration of P-113 used in the test compositions, a concentration of 0.01% (0.064 mM), the oxidation susceptible amino acids in P-113 are maximally protected at a level of about 0.2% methionine. The 48 hour data shows additional degradation of P-113, but only slightly above that seen after 24 hours.

The study of Examples 1 and 2 utilizing hydrogen peroxide is a simulated accelerated condition with extremely high levels of oxidative stress. In typical storage conditions where a composition is exposed to residual oxidants in formulation excipients and to environmental levels of oxygen, the oxidative stress is much lower than that artificially employed in the study. Therefore, the data in the Examples showing inhibition of oxidation when a composition is exposed to such abnormally high oxidation stresses clearly establishes that methionine is an effective antioxidant for polypeptides lacking methionine residues.

Further modifications, uses, and applications of the invention described herein will be apparent to those skilled in the art. It is intended that such modifications be encompassed in the following claims.

The invention claimed is:

1. A method for inhibiting oxidation of a polypeptide having an amino acid sequence that does not include a methionine residue comprising combining the polypeptide and free methionine in a liquid or semi-solid composition to obtain a composition comprising the polypeptide and the free methionine, wherein the free methionine that is combined in the composition is in an amount and for a time sufficient to inhibit oxidation of the polypeptide.

2. The method of claim 1 wherein the composition is an aqueous solution.

3. The method of claim 1 wherein the composition is an oil-in-water emulsion.

4. The method of claim 1 wherein the molar ratio of free methionine:polypeptide in the composition is 10:1 or higher.

5. The method of claim 1 wherein the molar ratio of free methionine:polypeptide in the composition is 20:1 or higher.

6. The method of claim 1 wherein the molar ratio is 100:1 or higher.

7. The method of claim 1 wherein the molar ratio is 200:1 or higher.

8. The method of claim 1 wherein the composition comprises a gelling agent.

9. The method of claim 8 wherein the gelling agent is selected from the group consisting of cellulosic polymers and carboxyvinyl polymers.

10. The method of claim 1 wherein the composition is free of polypeptides that have an amino acid sequence that contains methionine.

11. The method of claim 1 wherein the polypeptide and the free methionine are combined in the composition for a period of at least 24 hours.

12. The method of claim 11 wherein the polypeptide and the free methionine are combined in the composition for a period of at least 48 hours.

* * * * *